(12) United States Patent
Govari et al.

(10) Patent No.: US 10,314,507 B2
(45) Date of Patent: Jun. 11, 2019

(54) ASIC WITH SWITCHING NOISE REDUCTION

(71) Applicant: BIOSENSE WEBSTER (ISRAEL) LTD., Yokneam (IL)

(72) Inventors: Assaf Govari, Haifa (IL); Andres Claudio Altmann, Haifa (IL); Yaron Ephrath, Haifa (IL); Oleg Khudish, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 94 days.

(21) Appl. No.: 15/350,236

(22) Filed: Nov. 14, 2016

(65) Prior Publication Data

US 2018/0132749 A1    May 17, 2018

(51) Int. Cl.
| | |
|---|---|
| *A61B 5/04* | (2006.01) |
| *A61B 5/0428* | (2006.01) |
| *A61B 5/042* | (2006.01) |
| *A61B 5/00* | (2006.01) |
| *A61B 18/14* | (2006.01) |
| *A61B 5/0408* | (2006.01) |
| *A61B 18/00* | (2006.01) |

(52) U.S. Cl.
CPC ............ *A61B 5/04288* (2013.01); *A61B 5/00* (2013.01); *A61B 5/0408* (2013.01); *A61B 5/0422* (2013.01); *A61B 5/0428* (2013.01); *A61B 5/04085* (2013.01); *A61B 5/6858* (2013.01); *A61B 5/6859* (2013.01); *A61B 5/7203* (2013.01); *A61B 5/7225* (2013.01); *A61B 18/1492* (2013.01); *A61B 5/042* (2013.01); *A61B 2018/00267* (2013.01); *A61B 2018/00351* (2013.01); *A61B 2018/00577* (2013.01); *A61B 2018/00839* (2013.01); *A61B 2560/045* (2013.01)

(58) Field of Classification Search
CPC .. A61B 5/04288; A61B 5/0428; A61B 5/7203
See application file for complete search history.

(56) References Cited

U.S. PATENT DOCUMENTS

| | | | |
|---|---|---|---|
| 4,751,931 A | 6/1988 | Briller | |
| 5,042,499 A | 8/1991 | Frank et al. | |
| 5,231,990 A | 8/1993 | Gauglitz | |
| 5,337,230 A | 8/1994 | Baumgartner et al. | |

(Continued)

FOREIGN PATENT DOCUMENTS

JP    2000 059217 A    2/2000

OTHER PUBLICATIONS

Extended European Search Report for corresponding European application No. 17201290.8, dated Mar. 23, 2018.

*Primary Examiner* — Eric D. Bertram
(74) *Attorney, Agent, or Firm* — Notaro, Michalos & Zaccaria P.C.

(57) ABSTRACT

Medical catheterization is carried out by receiving a plurality of analog bioelectric signals in respective channels and multiplexing the bioelectric signals in respective selection events. The selection events comprise making a first connection with a reference voltage, thereafter breaking the first connection and making a second connection with one of the bioelectric signals. The method is further carried out by outputting the multiplexed bioelectric signals to an analog-to-digital converter.

4 Claims, 4 Drawing Sheets

(56) References Cited

U.S. PATENT DOCUMENTS

| | | |
|---|---|---|
| 5,555,888 A | 9/1996 | Brewer et al. |
| 6,093,186 A | 7/2000 | Goble |
| 6,226,542 B1 | 5/2001 | Hundt et al. |
| 6,301,496 B1 | 10/2001 | Reisfeld |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 8,185,191 B1 | 5/2012 | Shapiro et al. |
| 8,478,383 B2 | 7/2013 | Bar-Tal et al. |
| 8,697,205 B2 | 4/2014 | Dowling |
| 8,934,965 B2 | 1/2015 | Rogers et al. |
| 9,081,163 B2 | 7/2015 | Bradley et al. |
| 2003/0028173 A1 | 2/2003 | Forsberg |
| 2008/0243013 A1 | 10/2008 | Yanai et al. |
| 2014/0371563 A1 | 12/2014 | Lichtenstein |
| 2015/0160425 A1 | 6/2015 | Bradley et al. |
| 2015/0164354 A1 | 6/2015 | Parker et al. |
| 2016/0008062 A1* | 1/2016 | Gelbart .............. A61B 18/1492 600/483 |
| 2016/0038657 A1 | 2/2016 | Lareau et al. |

\* cited by examiner

ASIC WITH SWITCHING NOISE REDUCTION

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to measurement of bioelectric currents. More particularly, this invention relates to systems for recording bioelectric signals from the heart using multiple channels.

2. Description of the Related Art

The meanings of certain acronyms and abbreviations used herein are given in Table 1.

TABLE 1

Acronyms and Abbreviations

| | |
|---|---|
| ECG | Electrocardiogram |
| ASIC | Application Specific Integrated Circuit |
| DPDT | Double Pole Double Throw |
| MUX | Multiplexer |

A typical ECG system, such as the CARTO® 3 System, available from Biosense Webster, Inc., 3333 Diamond Canyon Road, Diamond Bar, Calif. 91765, receives multiple analog ECG signals simultaneously. Rather than digitizing each of the signals with a separate analog-to-digital-converter (A/D), the signals may be transferred via a multiplexer to a single digital-analog-converter. The output of the single digital-analog-converter is then de-multiplexed to recover the separate digitized signals.

Multiplexers are known for dealing with separate signals. For example, U.S. Pat. No. 5,337,230 to Baumgartner et al. proposes a mixed analog and digital integrated circuit with features, which constitute a front end for physiological signal instrumentation. In one embodiment five 16-bit shift registers each provide 16 bits clocked out during each sample to a digital multiplexer.

In another example, U.S. Pat. No. 5,231,990 to Gauglitz describes an application specific integrated circuit (ASIC) for physiological monitoring that has multiple inputs and outputs in which multiple ASICs can be coupled together to expand the number of channels being monitored. Each ASIC has multiple inputs that may be coupled to the patient and analog expansion inputs to accept signals from other ASICs. The ASIC includes an analog multiplexer and sample/hold circuit to interface with an external analog to digital converter.

However, multiplexing the incoming ECG signals introduces switching noise into the signal output from the multiplexer. Some existing systems have attempted to mitigate this problem by making the analog channel differential and by using common-mode feedback at every stage of amplification. In another approach U.S. Patent Application Publication No. 2015/0164354 describes an electrode configuration that proposes to reduce artifact induced in a single metallic electrode. The electrode is composed of two or more smaller electrodes that can be disconnected during a stimulation phase, and reconnected during a measurement phase. The electrode may be segmented, individual current sources being provided for each segment, forcing the current in the segments to match, and thereby reducing artifact.

SUMMARY OF THE INVENTION

According to disclosed embodiments of the invention, an ASIC multiplexes analog ECG signals from multiple channels for application in a physiologic monitoring system. In order to reduce the switching noise associated with the multiplexed signals, an electronic DPDT (double pole double throw) switch is incorporated into the multiplexer. The multiplexer switches between the ECG signals. At each switching event the DPDT switch first connects to a reference signal, and then to the incoming ECG signal.

There is provided according to embodiments of the invention a method, which is carried out by receiving a plurality of analog bioelectric signals in respective channels and multiplexing the bioelectric signals in respective selection events. The selection events comprise making a first connection with a reference voltage, thereafter breaking the first connection and making a second connection with one of the bioelectric signals. The method is further carried out by outputting the multiplexed bioelectric signals to an analog-to-digital converter.

According to one aspect of the method, making a first connection and making a second connection are accomplished by placing a double pole double throw switch in a first position and a second position, respectively.

A further aspect of the method includes connecting a Wilson central terminal to a first input of a differential amplifier, connecting one of the bioelectric signals to a second input of the differential amplifier, and linking first and second outputs of the differential amplifier to the double pole double throw switch.

Yet another aspect of the method includes interposing a buffer between the differential amplifier and the double pole double throw switch.

There is further provided according to embodiments of the invention an apparatus including a catheter having an elongated distal portion and a plurality of electrodes on the distal portion for reading bioelectric signals. The apparatus includes a multiplexor having inputs connected to respective ones of the electrodes. A switch has a first input terminal connected to a reference signal, a second input terminal linked to the output of the multiplexor. Control circuitry linked to the switch and the multiplexor is operative to make a first connection between the output terminal of the switch and the reference signal via the first input terminal of the switch, and thereafter to break the first connection and to make a second connection between the output terminal of the switch and the output of the multiplexor via the second input terminal of the switch.

In another aspect of the apparatus, the bioelectric signals are analog signals, and an analog-to-digital converter is connected to the output terminal of the switch and linked to a processor.

According to an additional aspect of the apparatus, the switch is a double pole double throw switch.

According to another aspect of the apparatus, the control circuitry includes a differential amplifier having first and second inputs connected to the first and second input terminals of the switch, respectively. The first input of the differential amplifier is connected to a Wilson central terminal, and the second input of the differential amplifier is linked to one of the bioelectric signals.

According to one aspect of the apparatus, the Wilson central terminal is connected to a dynamic offset voltage.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

The terms "link", "links", "couple" and "couples" are intended to mean either an indirect or direct connection. Thus, if a first device couples to a second device, that connection may be through a direct connection, or through an indirect connection via other devices and connections.
Overview.

Figure 1:
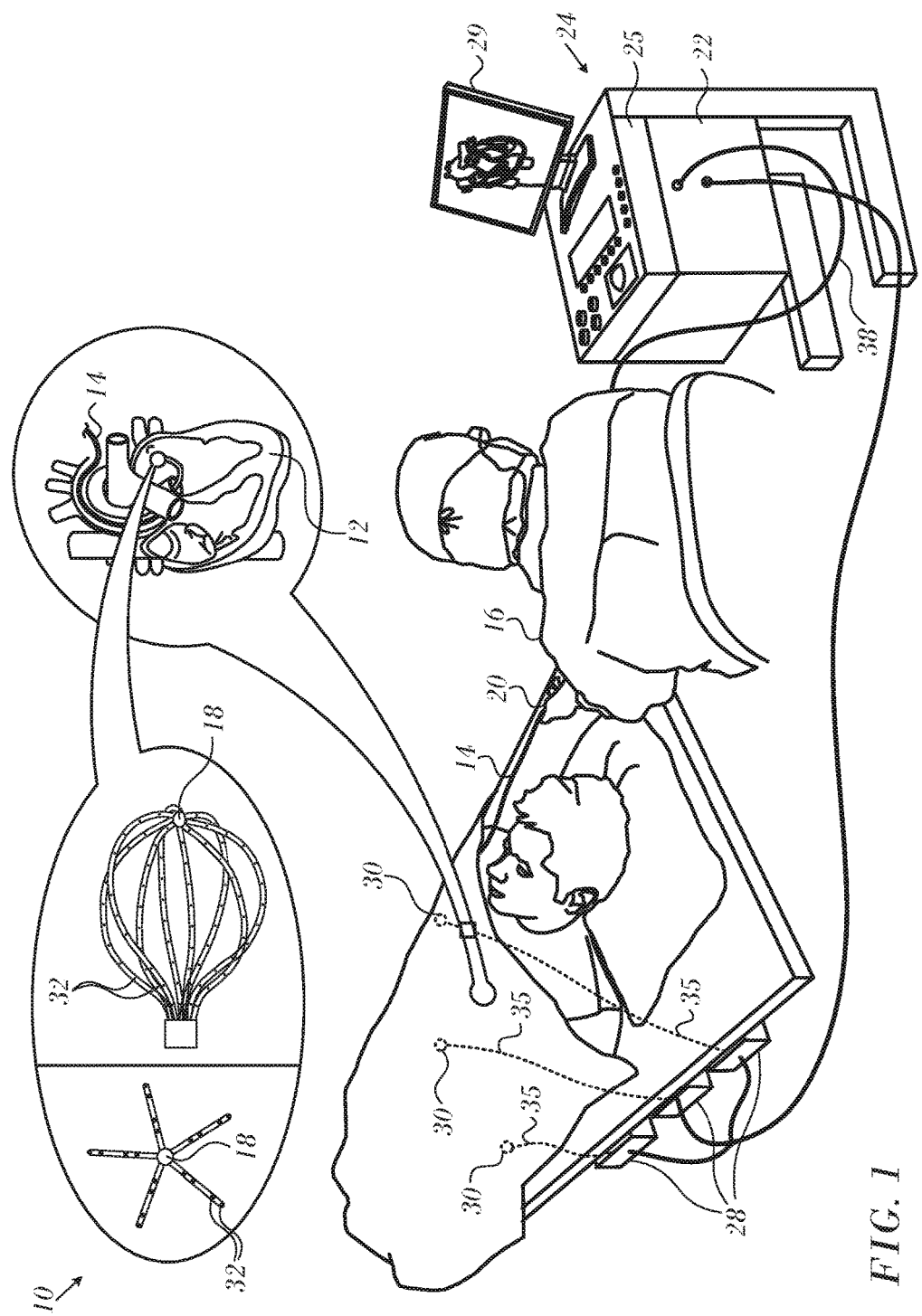
FIG. 1 is a pictorial illustration of an exemplary system for performing procedures on a heart of a living subject, which is constructed and operative in accordance with a disclosed embodiment of the invention.

Turning now to the drawings, reference is initially made to FIG. 1, which is a pictorial illustration of an exemplary system 10 for performing procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. It should be understood that the principles of the invention are not limited to systems such as the system 10, but may be applied to other systems in which bioelectric signals are received via multiple channels.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a multi-electrode catheter, which can be a basket catheter as shown in the right portion of the balloon or a spline catheter as shown in the left portion. In any case there are multiple electrodes 32, which are used as sensing electrodes and have known locations on the basket or spline, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an ECG monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. The system 10 may receive image data from an external imaging modality, such as an MRI unit or the like and includes image processors that can be incorporated in or invoked by the processor 22 for generating and displaying images.

In a typical application of the system 10 a chamber of the heart is catheterized conventionally with a multi-electrode catheter. Either a multi-spline catheter of a basket catheter is suitable. In such catheters each electrode has a known position on the basket or the splines as the case may be. Once the catheter is in place, if desired a current position map may be constructed using location sensors in the catheter, for example magnetic location sensors or using impedance measurements as noted above. The location of each of the electrodes in the heart is known from the current position map, or can be determined using imaging techniques. A typical multi-spline catheter used with the system 10 has, on its distal end, 60 electrodes, which acquire 60 sets of ECG signals from 60 points in the heart. The electrodes are distributed over the splines, assumed herein to be eight splines. The signals may be presented as 60 voltage vs time graphs. Other suitable catheters may have relatively more or fewer electrodes.

Figure 2:
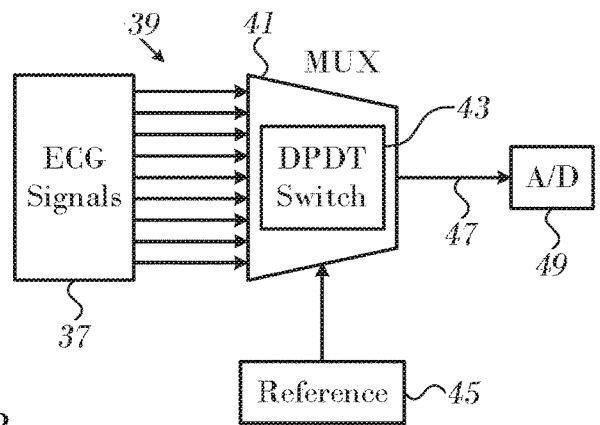
FIG. 2 is a schematic of a multiplexed arrangement for processing multi-channel ECG signals in accordance with an embodiment of the invention.

Reference is now made to FIG. 2, which is a schematic of a multiplexed arrangement for processing multi-channel ECG signals in accordance with an embodiment of the invention. A terminal 37, comprising analog ECG signals in multiple channels 39, typically from respective electrodes of a multichannel catheter, such as shown in FIG. 1, is input to a multiplexer 41 (MUX), which selects each of the channels 39 in turn. Included in the multiplexer 41 is a double pole double throw (DPDT) switch 43, which first connects to a reference signal 45 and then to the selected channel 39. Output 47 is sent to an analog-to-digital converter 49.

Figure 3:
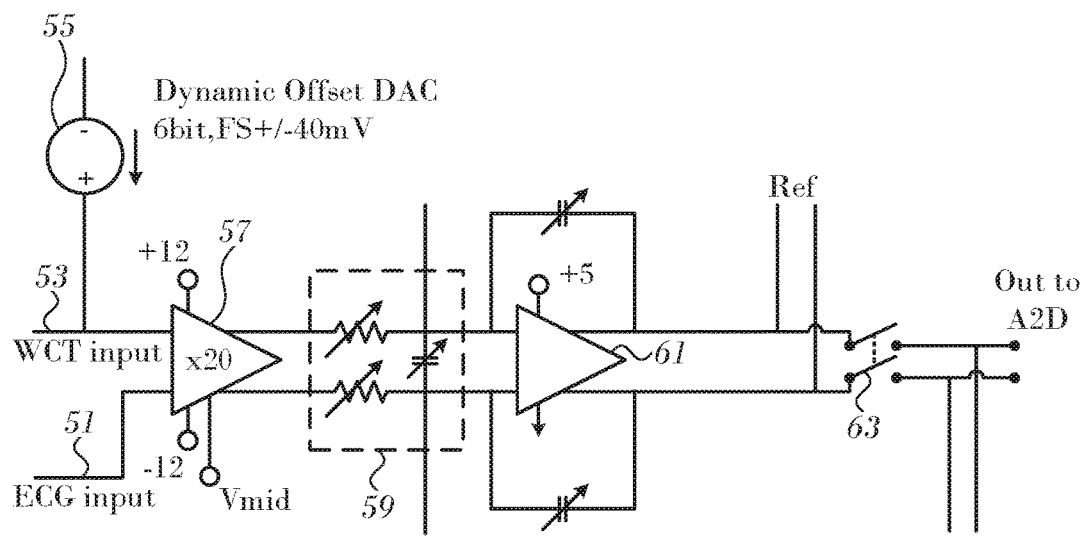
FIG. 3 is an electrical schematic of one of the channels shown in FIG. 2 in accordance with an embodiment of the invention.

Reference is now made to FIG. 3, which is an electrical schematic of one of the channels 39 (FIG. 2) in accordance with an embodiment of the invention. An ECG input 51 and a reference input 53, typically taken from a Wilson central terminal and modified by dynamic offset 55 are submitted to a differential amplifier 57, thence through a low pass filter 59 and buffer 61. Alternatively, the reference input 53 can be the average of all the electrodes. The buffer output is presented to a DPDT switch 63. In a closed position the DPDT switch 63 conveys the outputs of the buffer 61 to an analog-to-digital converter. In an open position the output of the buffer is held at a reference voltage.

Figure 4:
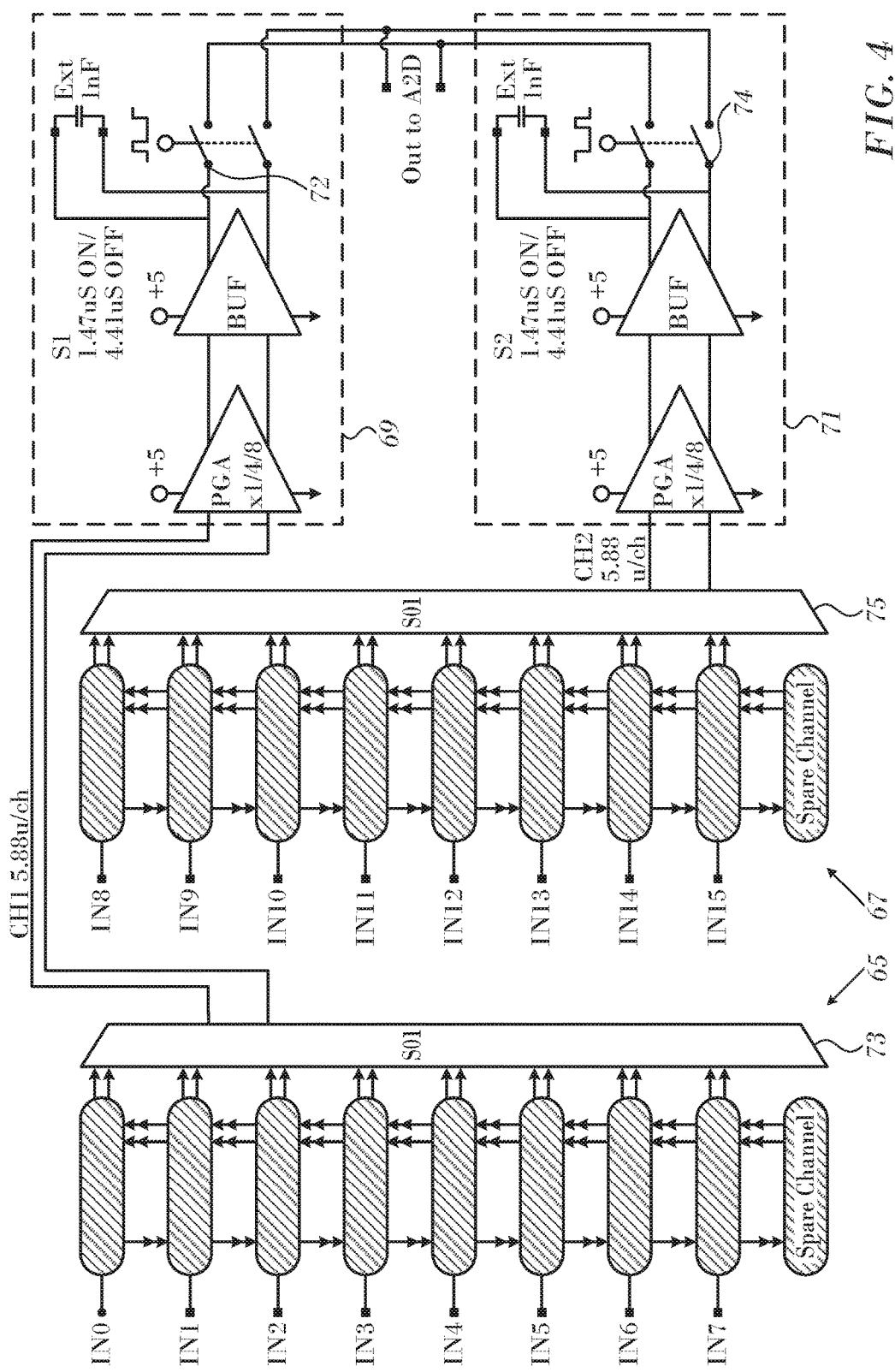
FIG. 4 is an electrical schematic of a portion of an electrical circuit showing multiple channels in accordance with an embodiment of the invention.

Reference is now made to FIG. 4, which is an electrical schematic of a portion of an ASIC showing multiple channels in accordance with an embodiment of the invention. Sixteen channels labeled IN0-IN15 are arranged in two banks 65, 67 that connect via selectors 73, 75 to switching circuits 69, 71. The circuits 69, 71 are similar to the circuit described with respect to FIG. 3, in which DPDT switches 72, 74 have the function of DPDT switch 63 (FIG. 3). Each channel is selected for 5.88 μs, switched on for 1.47 μs (¼ duty cycle) and off for 4.41 μs, typically 20,000 samples per channel are acquired. Thus, the analog-to-digital converter needs to sample at 640,000 samples/sec. (Note that the analog-to-digital converter services both of the circuits 69, 74). The settling time must be less than 1.47 μs.

Figure 5:
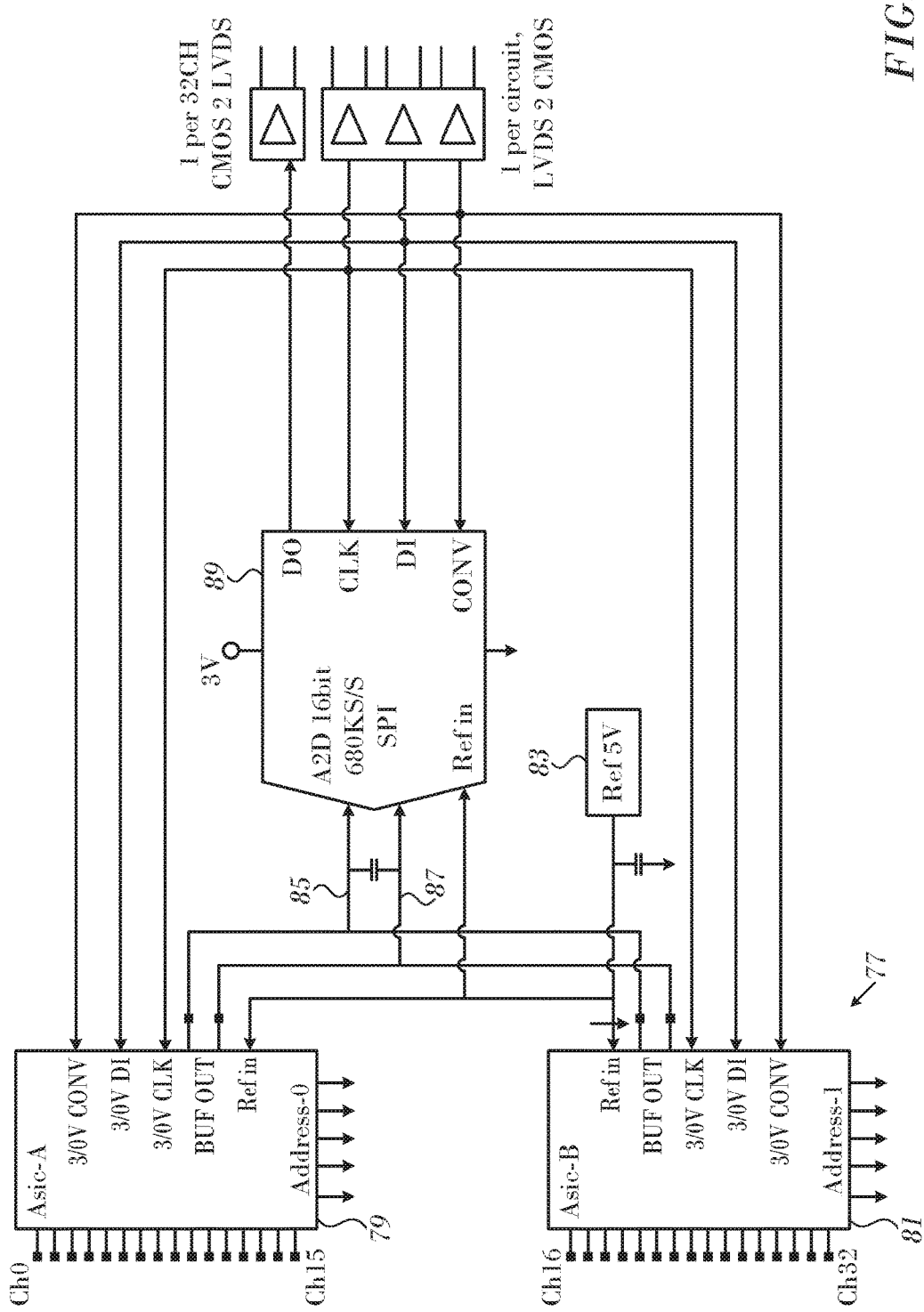
FIG. 5 is an electrical schematic of an electrical circuit in accordance with an embodiment of the invention.

Reference is now made to FIG. 5, which is an electrical schematic of an ASIC 77 in accordance with an embodiment of the invention. Two modules 79, 81 each receive 16 channels from a cardiac catheter (not shown) as input, denoted Ch0 . . . Ch15, and CH16 . . . Ch32, respectively. A five volt reference 83 is connected to each of the modules 79, 81. A selected channel from the modules 79, 81 is output on lines 85, 87 to analog-to-digital converter 89. The modules 79, 81 include logical circuitry to switch the outputs on lines 85, 87. Both the reference 83 and the signal from the selected channel on lines 85, 87 are switched into the analog-to-digital converter 89. As explained above in the discussion of FIG. 3 and FIG. 4, at each switching event DPDT switches (not shown) included in the ASIC 77 first connect to a reference signal, and then to the incoming ECG signal to prevent charge injection and allow for fast settling time.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus comprising
a catheter having an elongated distal portion;
a plurality of electrodes on the distal portion for reading bioelectric signals:
a multiplexor having inputs connected to respective ones of the electrodes and having an output;
a switch having a first input terminal connected to a reference signal, a second input terminal linked to the output of the multiplexor, and an output terminal; and
control circuitry linked to the switch and the multiplexor and operative to make a first connection between the output terminal of the switch and the reference signal via the first input terminal of the switch; and thereafter to break the first connection and to make a second connection between the output terminal of the switch and the output of the multiplexor via the second input terminal of the switch,
wherein the control circuitry comprises a differential amplifier having first and second inputs and having first and second outputs connected to the first and second input terminals of the switch, respectively, wherein the first input of the differential amplifier is connected to a Wilson central terminal, and the second input of the differential amplifier is linked to one of the bioelectric signals.

2. The apparatus according to claim 1, wherein the bioelectric signals are analog signals, further comprising an analog-to-digital converter connected to the output terminal of the switch and linked to a processor.

3. The apparatus according to claim 1, wherein the switch is a double pole double throw switch.

4. The apparatus according to claim 1, wherein the Wilson central terminal is connected to a dynamic offset voltage.

* * * * *